United States Patent
Bonnet et al.

(10) Patent No.: US 6,830,548 B2
(45) Date of Patent: Dec. 14, 2004

(54) ACTIVE MEDICAL DEVICE ABLE TO DIAGNOSE A PATIENT RESPIRATORY PROFILE

(75) Inventors: Jean-Luc Bonnet, Olivet (FR); Marcel Limousin, Paris (FR)

(73) Assignee: ELA Medical S.A., Montrouge (FR)

( * ) Notice: Subject to any disclaimer, the term of this patent is extended or adjusted under 35 U.S.C. 154(b) by 37 days.

(21) Appl. No.: 10/255,144

(22) Filed: Sep. 24, 2002

(65) Prior Publication Data

US 2003/0078619 A1 Apr. 24, 2003

(30) Foreign Application Priority Data

Sep. 24, 2001 (FR) .............................................. 01 12239

(51) Int. Cl.[7] .................................................. A61B 5/08
(52) U.S. Cl. ........................... 600/529; 607/20; 607/28; 600/536
(58) Field of Search ............................. 607/28, 42, 62, 607/63, 2–6, 9, 17–20; 600/529–543, 50 B, 547, 508, 513

(56) References Cited

U.S. PATENT DOCUMENTS

| | | | |
|---|---|---|---|
| 4,827,935 A | | 5/1989 | Geddes et al. |
| 5,245,995 A | | 9/1993 | Sullivan et al. |
| 5,303,702 A | * | 4/1994 | Bonnet et al. ................ 607/20 |
| 5,974,340 A | | 10/1999 | Kadhiresan |
| 6,076,015 A | * | 6/2000 | Hartley et al. ................ 607/20 |
| 6,415,183 B1 | * | 7/2002 | Scheiner et al. .............. 607/42 |
| 6,589,188 B1 | * | 7/2003 | Street et al. ................. 600/538 |
| 6,600,949 B1 | * | 7/2003 | Turcott ....................... 600/518 |
| 6,641,542 B2 | * | 11/2003 | Cho et al. ................... 600/529 |

FOREIGN PATENT DOCUMENTS

| | | | |
|---|---|---|---|
| WO | WO 93/02744 | 2/1993 | ........... A61N/1/36 |
| WO | WO 98/33554 | 8/1998 | ........... A61N/1/37 |
| WO | WO 01/41868 A1 | 6/2001 | ........... A61N/1/36 |

* cited by examiner

Primary Examiner—Robert L. Nasser
Assistant Examiner—Patricia Mallari
(74) Attorney, Agent, or Firm—Orrick, Herrington & Sutcliffe LLP

(57) ABSTRACT

An active medical device to diagnose a patient respiratory profile. This device is able to measure respiratory activity and deliver a signal (26) representative of the periodicity and amplitude of the successive respiratory cycles of the patient, in particular, a of minute ventilation (MV) signal. The device is able to analyze the aforementioned signal and discriminate between various types of respiratory profiles, in particular, to diagnose a respiratory profile of the Cheyne-Stokes type. This is achieved by detecting an alternation of respiratory cycles of hyperventilation (20) separated by periods of respiratory pause (22) or periods of hypoventilation or normal ventilation (24) and, in the latter case, to discriminate between periods of respiratory pause, corresponding to a profile of the Cheyne-Stokes (CSR) type, and periods of hypoventilation or normal ventilation, corresponding to a profile of the periodic breathing (PB) type.

5 Claims, 3 Drawing Sheets

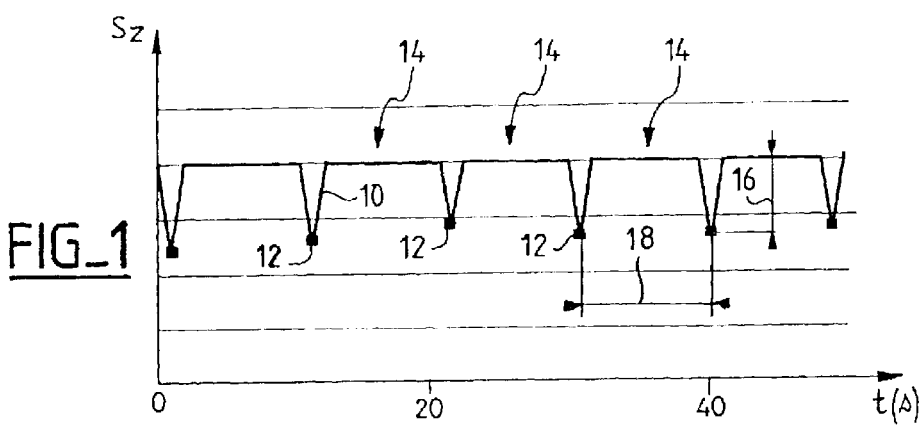
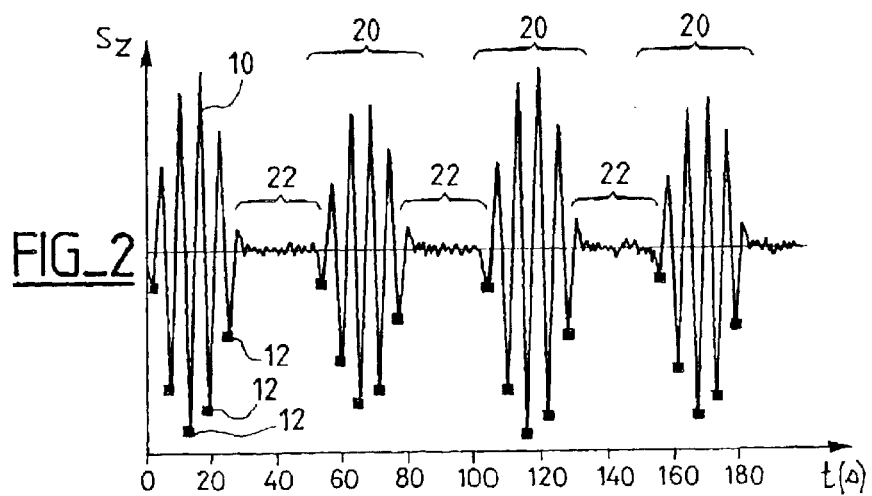
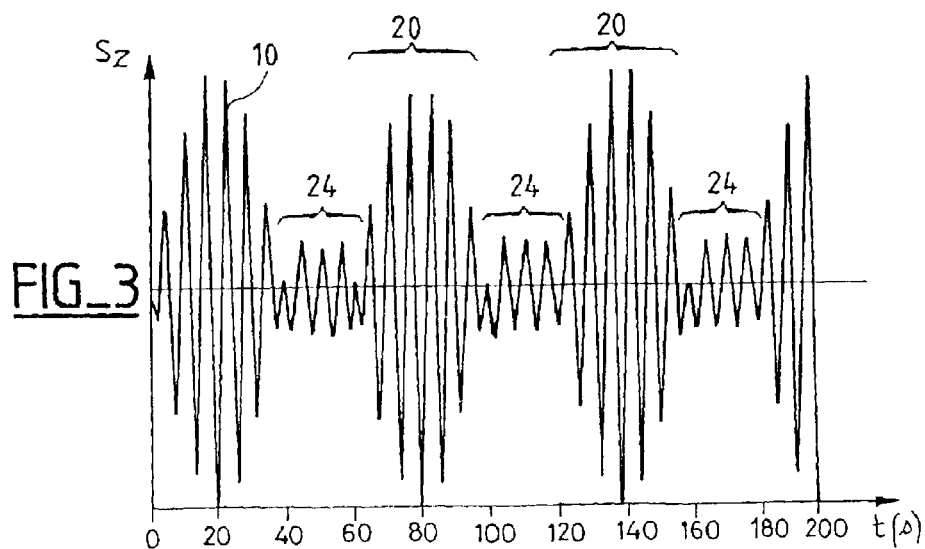

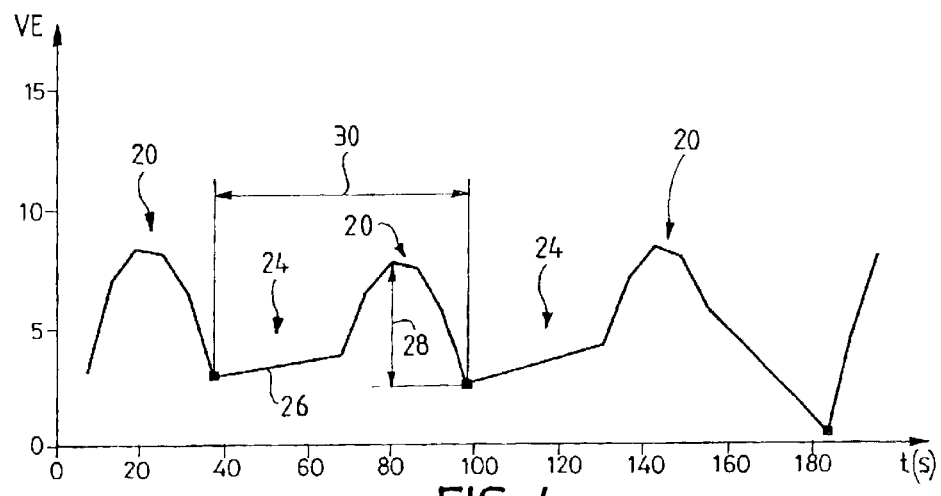
FIG_4
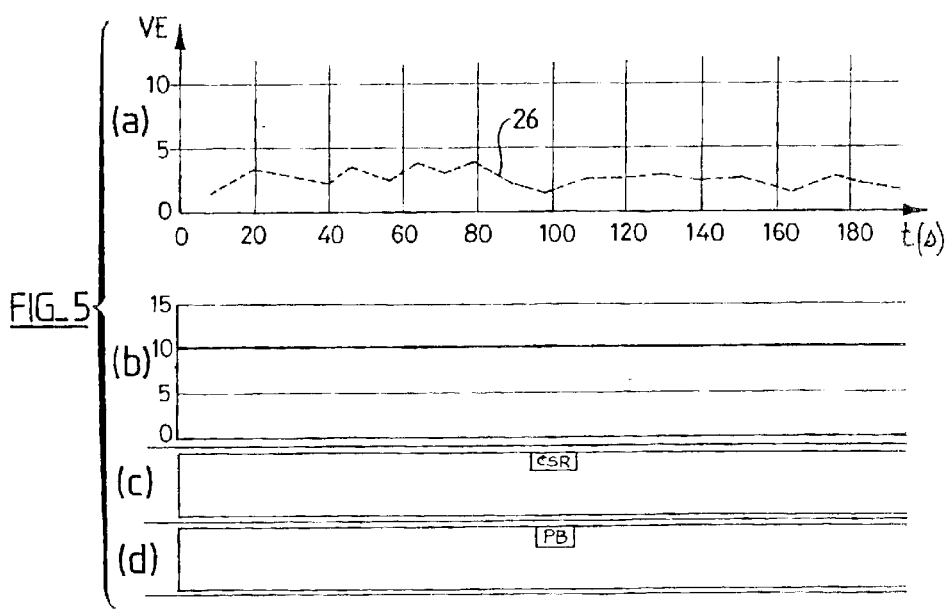
FIG_5

ACTIVE MEDICAL DEVICE ABLE TO DIAGNOSE A PATIENT RESPIRATORY PROFILE

FIELD OF THE INVENTION

The present invention relates to "active medical devices" as such devices are defined by the Jul. 12, 1993 directive 93/42/CEE of the Council of the European Communities, and more particularly to the diagnosis of respiratory frequency and amplitude disorders by such devices.

The present invention will be more particularly described in the case of active implantable medical devices such as pacemaker, defibrillator and/or cardiovertor devices that are also able to deliver to the heart pulses of low energy for the treatment of heartbeat rate disorders. It should be understood, however, that the device being implanted is not in any way restrictive of the invention, and that the teaching of the invention is directly applicable to many diagnostic and/or therapeutic types of active medical devices.

BACKGROUND OF THE INVENTION

Patients suffering from cardiac insufficiency also frequently present a disturbed or abnormal ventilation (respiration) pattern. The incidence of sleep apnea is abnormally increased, and the respiratory profile is also often modified.

Among other things, these patients can present periodic ventiliation profiles with phases of hyperventilation alternating with either phases of normal breathing or hypoventilation, a disorder that is known by the name of "periodic breathing" (or Periodic Breathing ("PB"), or of respiratory pauses, a disorder that is known by the name of "dyspnea of Cheyne-Stokes" or "Cheyne-Stokes breathing" (or, Cheyne-Stokes Respiration ("CSR")). The various alternate phases each have a duration in a range of a few respiratory cycles to a few tens of respiratory cycles, i.e., of a few seconds or tens of seconds (even to a duration exceeding a minute).

The diagnosis of this type of breathing is a useful action that can make it possible to follow better the patients and to adapt their treatment as appropriate. In this regard, clinical study has indeed shown that an improvement of the cardiac function can make a CSR disappear. More precisely, it has been shown that CSR disappears gradually with an improvement of the left ventricular function. The CSR can, in this regard, be considered as a symptom indicating the effectiveness of the cardiac therapy applied.

Conversely, because CSR itself causes symptoms and thus can worsen the performance of an insufficient heart, it is important to be able to detect the presence of CSR and to evaluate its significance. The reduction of CSR (either by an improvement of the cardiac function, or by another type of treatment, for example, medication) can prevent the development of night cardiovascular dysfunction, reduce insomnia and the number of night wakeups. This action can improve the diurnal function and quality of life of the patient.

One of the goals of the present invention is to propose an active medical device that is able to detect the presence of a respiratory disorder, in particular of the CSR type, and to operate a discrimination between the various types of profiles (e.g., PB or CSR), in an automatic and reliable way.

The traditional diagnostic means is by use of polysomnography, an exhaustive examination that typically requires an over-night hospitalization. Considering its cost, this examination is seldom proposed, especially in the beginning phase of the disease. Furthermore, difficulties in using polysomnography do not allow a regular follow-up that is needed to evaluate the evolution of the symptoms over time.

It is known from International Patent Publication WO-A-98/33554 to have an active implantable device medical that is able to follow the respiratory frequency by an analysis of the intracorporal impedance. However, the aim set by this device is to provide an indicator of the occurrence of a pulmonary edema, with the acceleration of the respiration rate being a traditional symptom of this pathology. This device analyzes only the respiration rate (frequency) and, lacking a fine analysis of ventilation, is not able to distinguish types of ventilation profiles, such as the PB or CSR type disorders.

It also is known from EP-A-0 493 222 and its corresponding U.S. Pat. No. 5,303,702, commonly assigned herewith to Ela Medical to have a pacemaker including means for measuring the respiratory activity of the patient, more specifically the minute ventilation, which parameter is used to control the stimulation pulse frequency.

OBJECTS AND SUMMARY OF THE INVENTION

A device in accordance with the present invention is of the type known according to the EP-A-0 493 222 and U.S. Pat. No. 5,303,702 mentioned above, i.e., an active medical device including means for measuring patient respiratory activity and able to deliver a signal representative of the periodicity and amplitude of the successive respiratory cycles of the patient.

According to the invention, the device also includes discriminating means, able to analyze the aforementioned respiratory signal and to operate a discrimination between various types of respiratory profiles.

In a preferred embodiment, the discriminating means include means for detecting an alternation of hyperventilation respiratory cycles separated by respiratory pause periods or hypoventilation periods, and to discriminate between periods of respiratory pause, hypoventilation or normal ventilation. Preferably, the means for discriminating includes means for analyzing the variations to the second order of the aforesaid signal. In particular, the discriminating means is able to diagnose a respiratory profile of Cheyne-Stokes type.

Preferably also the aforementioned respiratory signal is a minute ventilation signal, and, more preferably, can be the same minute ventilation signal that is known to be used to control the stimulation pulse frequency in rate responsive cardiac pacemakers.

The analyzing means can in particular include means able to detect peaks of the aforesaid respiratory signal and to evaluate the interval between successive peaks, and in particular evaluate the interval relative to a threshold value, to compare the interval(s) between successive peaks and to diagnose a respiratory profile of the Cheyne-Stokes type only for these intervals having a duration higher than the threshold value.

In a preferred embodiment, the comparison is operated only if the signal amplitude value is higher than a given minimal value, and/or the comparison is made only for values of intervals ranging between a minimal value and a maximum value data.

In one embodiment, the invention is directed to an active medical device of the pacemaker, defibrillator, cardiovertor and/or multisite device type, comprising:

means for measuring respiratory activity and providing a signal representative of the periodicity and amplitude of a plurality of successive respiratory cycles of a patient, discriminating means for analyzing the signal, discriminating between various types of respiratory profiles, and diagnosing a Cheyne-Stokes type respiratory profile, said discriminating means comprising:

means for detecting in said signal an alternation of a hyperventilation respiratory cycle separated by one of a respiratory pause period, a hypoventilation period, and a normal ventilation period, and second discriminating means, responsive to a detected alternation of a hyperventilation and a normal ventilation, for discriminating between a respiratory pause period and a hypoventilation period or a normal ventilation period by analysis of variation of a second order of said signal, said second discriminating means further comprising means for analyzing the variation of the second order of the signal by identifying a peak value of said signal and an interval between successive peak values.

Preferably, the discriminating means further comprises one or more of (1) means for comparing the interval between successive peaks to a threshold value, and diagnosing a Cheyne-Stokes type respiratory profile only for said interval having a duration greater than said threshold value, and (2) means for comparing the peak amplitude with a given minimal value and wherein the means for seeking peak values is responsive to seek a peak value in response to the amplitude value of the signal being greater than the given minimal value.

Also included may be a means for determining whether the interval value is between a minimal value and a maximum value, wherein the discriminating means comparison is operated only for values of intervals ranging between said minimal and maximum values. Further, the provided signal is preferably representative of the patient's minute ventilation.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings in which:

FIG. 1 is a chronogram (amptitude versus time) showing the short-term variations of an intracorporal impedance signal, in the case of a normal night ventilation;

FIGS. 2 and 3 are chronograms showing the longer-term variations of the impedance signal, for pathological CSR and PB type respiratory profiles respectively;

FIG. 4 is a chronogram showing the variations of the minute ventilation parameter obtained from an impedance signal of FIG. 3; and FIGS. 5, 6 and 7 are respectively chronograms showing, for various evolutions of the minute ventilation signal, the duration of the respiratory pauses eventually detected, as well as CSR or PB markers generated as necessary by the device.

DETAILED DESCRIPTION OF THE INVENTION

Figure 6:
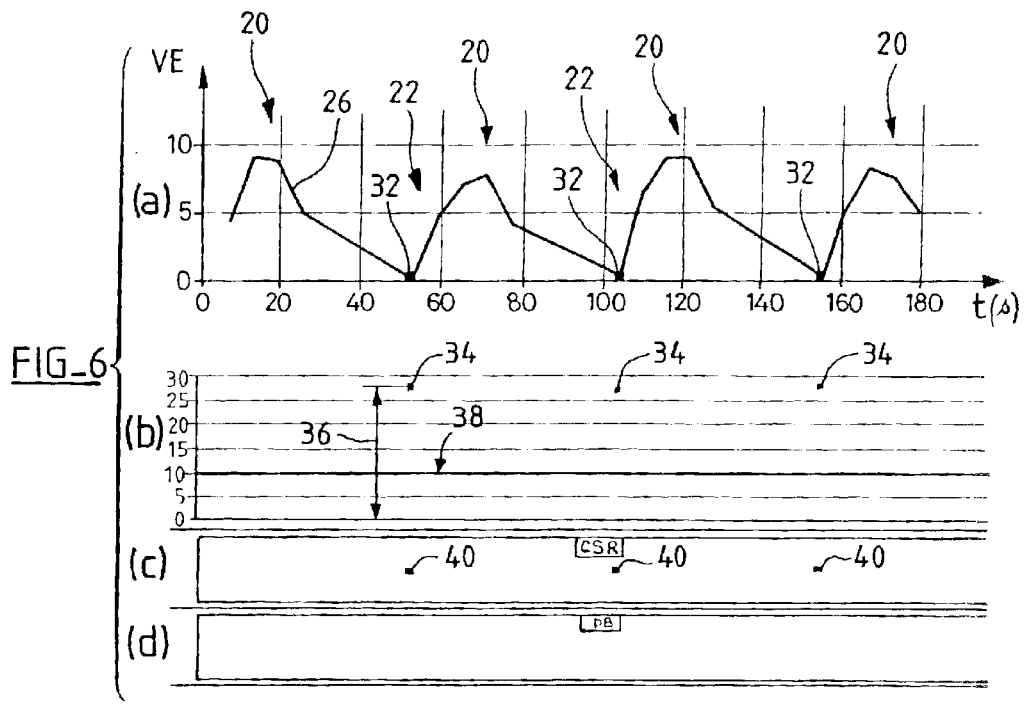

To seek pathologies of the PB or CSR type, and to operate a discrimination between these two types of respiratory profiles, the device of the present invention searches for a periodicity in the detected minute ventilation. The periodicity is measured starting from the amplitude and periodicity parameters of the successive respiratory cycles. The specific manner of deriving the respiratory signal and the particular signal derives are not important to the invention provided that the acquired signal has reflects the periodicity of the respiratory activity, and any suitable signal may be used.

The analysis from cycle to cycle is preferably carried out according to a standard method, for example, the method described in the EP-A-0 493 222 and U.S. Pat. No. 5,303,702 mentioned above. The person of ordinary skill in the art is referred to these documents for further details on a way that a signal representative of the respiratory activity may be collected and analyzed, in particular to derive from it of the minute ventilation information (MV).

The measurement of the respiratory activity is in itself well-known; it is typically carried out between two electrodes typically laid out in the rib cage, or between an electrode (for example, a stimulation electrode, if the implanted device is pacemaker) and a case of the implanted medical device. The impedance is measured by injection of a constant current of a few hundreds of microamperes, at a frequency of a few hertz, typically 8 Hz. This particular technique for example is described by Bonnet J. L., et al., "Measurement of Minute-Ventilation with Different DDDR Pacemaker Electrode Configurations", PACE, Vol. 21, 98, Part 1, and it is used in the Chorus™ RM 7034, Talent™ and Symphony products available from ELA Medical, Montrouge, France.

The device of a preferred embodiment of the invention employs this technique and thus produces successive impedance samples that, after filtering, produces an impedance signal Sz. A representative impedance signal Sz is illustrated at 10 on FIG. 1 (showing an increase in impedance corresponding to a reduction in the signal from the analog to digital converter, because of the presence of an inverter). The signal 10 presents impedance peaks 12, corresponding to the inspirations (the impedance increases by an increase of the volume of air in the lungs) separated by physiological pauses 14, corresponding to expiratory pauses.

The device isolates the peaks 16 of the impedance signal Sz, i.e., the troughs of the converted signal, and determines for each peak amplitude 16 a period 18 of the respiratory cycle. The respiratory amplitude corresponds to the volume of the current cycle, i.e., the quantity of air inspired; the relationship between the amplitude and the period measured in the same respiratory cycle is the measurement of minute ventilation MV. To eliminate the artifacts that would produce respiratory cycles that are too short and/or of too low an amplitude, only the periods and the amplitudes located inside a range of predetermined values are retained.

FIG. 2 shows an evolution, over a longer duration, of the impedance signal Sz in the case of a breathing of the Cheyne-Stokes (CSR) type. In this case, one observes typically rapid variations or spindles of hyperventilation 20, lasting approximately 3 to 30 respiratory cycles (approximately 6 to 75 seconds) separated by long respiratory pauses (apnea) 22, of a duration that may typically last from 5 to 70 seconds.

FIG. 3 is homologous with FIG. 2, in the case of breathing of a periodic breathing (PB) type. The profile here also is periodic, but the respiratory pauses 22 are replaced by simple periods of hypoventilation or normal ventilation 24.

The following discussion concerns the stage of analysis relevant to evaluating the variations over the long term. It should be understood that, the reference in the description to "variation to the first order" concerns the variations of the considered parameter (e.g., the impedance signal) during the same respiratory cycle, and references to "variation of the second order", are to the variations of minute ventilation MV over several successive cycles or tens of successive cycles. The following stage thus concerns seeking and analyzing a periodicity to the second order of the ventilation activity, revealing a profile of the PB or CSR type.

Figure 7:
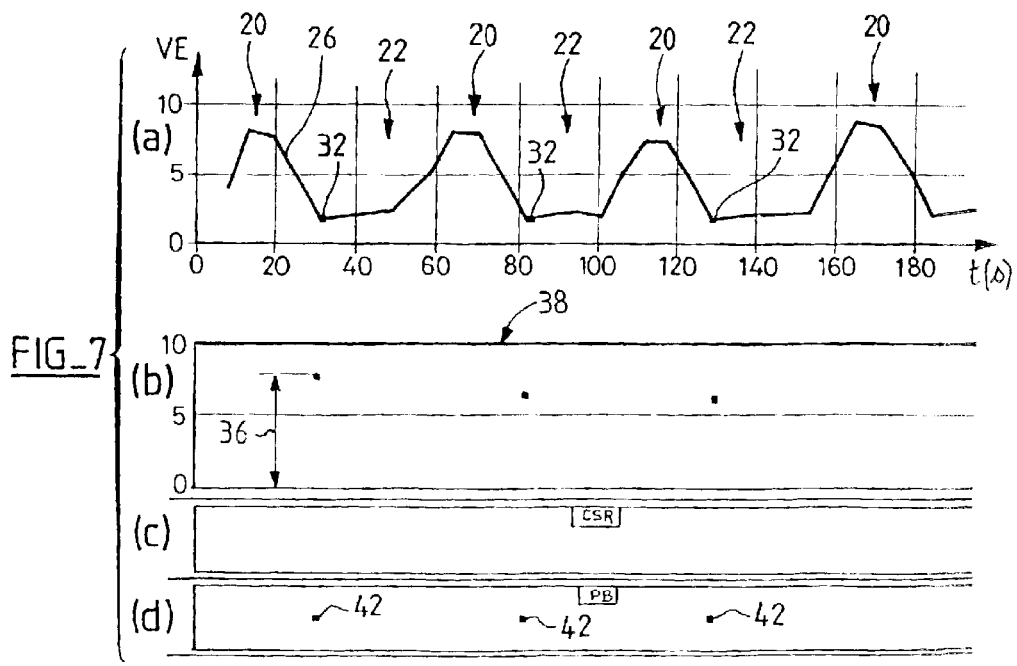

From the impedance signal indicated above, one evaluates the variations of minute ventilation MV during the time, as illustrated by signal 26 of FIG. 4 (and also by the line (a) of FIGS. 5 to 7).

In the case of breathing of the PB or CSR type, the minute ventilation presents, just as impedance signal Sz presents, an alternation of periods of hyperventilation 20 and respiratory pauses 22 (FIGS. 6 and 7) or periods of normal breathing or hypoventilation 24 (FIG. 4).

The device then evaluates amplitude 28 and period 30 of the variations of the second order of minute ventilation MV, by applying a preliminary selection so as to retain only the peaks presenting one minimal period (corresponding to the required periodicity of the successive phases, typically a 10 second minimum), and a limiting amplitude. According to the nature of breathing, the ventilation activity signal will be more or less cyclic. FIGS. 5 to 7 present the three following respective situations:

FIG. 5: normal breathing;

FIG. 6: abnormal breathing of CSR type, if present;

FIG. 7: abnormal breathing of PB type, if present.

The four chronograms of each of these figures illustrate:

line (a): variation over time of the of minute ventilation signal MV (this line corresponds to the signal illustrated also on FIG. 4);

line (b): for each peak of ventilation eventually found, the quantified representation of the longest respiratory period;

line (c): markers of a CSR diagnosis;

line (d): markers of a PB diagnosis.

In the case of a normal breathing (FIG. 5), no significant peak of ventilation is detected (taking into account the limits and amplitudes imposed by the algorithm) and no diagnosis is established (hence, there is an absence of a marker).

In the case of a breathing of the CSR type (FIG. 6), the minute ventilation signal 26 presents a succession of ventilation peaks 32, in spite of the limitation criteria envisaged by the algorithm (minimum and maximum duration of the cycle of the second order between two ventilation activity peaks), and a criterion of minimal amplitude on the variation to eliminate the cycles that are too long and/or of too low an amplitude, that would be the reflection of a normal breathing, low variation and long periodicity, as in the case of FIG. 5).

In this case, to differentiate between a PB and a CSR profile, the device analyzes the longest period of the cycle; this value is represented on the line (b) by an item 34 located at a level 36, located in the example illustrated between 25 and 30 seconds. This level 36 is compared with a minimal threshold 38, for example, a 10 second threshold, typically. If such is the case, as illustrated in FIG. 6, it is indeed an apnea, and its cycle is thus classified as CSR by recording of a corresponding marker 40 (line c) corresponding to a positive diagnosis of CSR.

Conversely, in the case of a rate/rhythm of the PB type, as illustrated in FIG. 7, a duration 36 of the longest respiratory period of the cycle is lower than threshold 38, fixed in this example at 10 seconds; the device thus establishes a positive diagnosis of PB (and not one of CSR) and provides an associated marker 42.

Suitable devices for which the present invention has application include, but are not limited to, for example, the Talent™ and Symphony™ brand of pacemakers available from Ela Médical, Montrouge, France. These devices are capable of receiving software instructions by telemetry, storing them in memory, and then executing those instructions to perform the functions described above in implementing the present invention, including the use of the minute ventilation signal acquired by the existing devices. The creation of suitable software instructions for controlling an implant to perform the aforementioned functions of the present invention are believed to be within the abilities of a person of ordinary skill in the art.

One skilled in the art will appreciate that the present invention can be practiced by other than the described embodiments, which are presented for purposes of illustration and not of limitation.

We claim:

1. An active medical device of the pacemaker, defibrillator, cardiovertor and/or multisite device type, comprising:

means for measuring respiratory activity and providing a signal representative of the periodicity and amplitude of a plurality of successive respiratory cycles of a patient, discriminating means for analyzing the signal, discriminating between various types of respiratory profiles, and diagnosing a Cheyne-Stokes type respiratory profile, said discriminating means comprising:

means for detecting in said signal an alternation of a hyperventilation respiratory cycle separated by one of a respiratory pause period, a hypoventilation period, and a normal ventilation period, and second discriminating means, responsive to a detected alternation of a hyperventilation and a normal ventilation, for discriminating between a respiratory pause period and a hypoventilation period or a normal ventilation period by analysis of variation of a second order of said signal, said second discriminating means further comprising means for analyzing the variation of the second order of the signal by identifying a peak value of said signal and an interval between successive peak values.

2. The device of claim 1, wherein the discriminating means further comprises means for comparing the interval between successive peaks to a threshold value, and diagnosing a Cheyne-Stokes type respiratory profile only for said interval having a duration greater than said threshold value.

3. The device of the claim 1, wherein the discriminating means further comprises means for comparing the peak amplitude with a given minimal value and wherein the means for analyzing the variation of the second order of the signal is responsive to seek a peak value in response to the amplitude value of the signal being greater than the given minimal value.

4. The device of the claim 2, further comprising means for determining whether the interval is between a minimal value and a maximum value, wherein the discriminating means comparison is operated only for values of intervals ranging between said minimal and maximum values.

5. The device of claim 1 wherein said provided signal is representative of the patient's minute ventilation.

* * * * *

UNITED STATES PATENT AND TRADEMARK OFFICE
CERTIFICATE OF CORRECTION

PATENT NO.      : 6,830,548 B2
APPLICATION NO. : 10/255144
DATED           : December 14, 2004
INVENTOR(S)     : Bonnet et al.

It is certified that error appears in the above-identified patent and that said Letters Patent is hereby corrected as shown below:

Title Page, Item (57) ABSTRACT

Line 5, after "in particular," "a of" should be changed to --of a--.

IN THE SPECIFICATION

Column 1, line 29–30, "ventiliation profiles" should be changed to --ventilation profiles--.

Column 2, line 8, after "active implantable," "device medical" should be changed to --medical device--; line 64, after "maximum value," delete "data.".

Column 4, line 4, after "signal" and before "are not important," "derives" should be changed to --derived--; line 14, after "to derive from it," delete "of.".

Column 5, line 32, after "variation over time of the" before "minute ventilation," delete "of.".

IN THE CLAIMS

Claim 5, line 1, between "claim 1" and "wherein," insert --,--.

Signed and Sealed this
Eighteenth Day of October, 2011

David J. Kappos
*Director of the United States Patent and Trademark Office*

UNITED STATES PATENT AND TRADEMARK OFFICE
CERTIFICATE OF CORRECTION

PATENT NO.         : 6,830,548 B2
APPLICATION NO.    : 10/255144
DATED              : December 14, 2004
INVENTOR(S)        : Bonnet et al.

It is certified that error appears in the above-identified patent and that said Letters Patent is hereby corrected as shown below:

Title Page, Item (57) ABSTRACT

Line 5, after "in particular," "a of" should be changed to --of a--.

IN THE SPECIFICATION

Column 1, line 29–30, "ventiliation profiles" should be changed to --ventilation profiles--.

Column 2, line 8, after "active implantable," "device medical" should be changed to --medical device--; line 64, after "maximum value," delete "data.".

Column 4, line 4, after "signal" and before "are not important," "derives" should be changed to --derived--; line 14, after "to derive from it," delete "of.".

Column 5, line 32, after "variation over time of the" before "minute ventilation," delete "of".

IN THE CLAIMS

Column 6, line 64 (Claim 5, line 1) between "claim 1" and "wherein," insert --,--.

This certificate supersedes the Certificate of Correction issued October 18, 2011.

Signed and Sealed this
Twenty-second Day of November, 2011

David J. Kappos
*Director of the United States Patent and Trademark Office*